US00PP32342P2

(12) United States Plant Patent

Solano Ramirez

(10) Patent No.: US PP32,342 P2
(45) Date of Patent: Oct. 13, 2020

(54) *COLEUS* PLANT NAMED 'BALFLAMSIRA'

(50) Latin Name: *Solenostemon scutellarioides*
Varietal Denomination: Balflamsira

(71) Applicant: Ball Horticultural Company, West Chicago, IL (US)

(72) Inventor: Rolando Solano Ramirez, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/873,289

(22) Filed: Mar. 11, 2020

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of Coleus plant named 'Balflamsira', characterized by its dark greyed-red and deep yellow-green colored foliage, and moderately vigorous, upright growth habit, is disclosed.

1 Drawing Sheet

Latin name of genus and species of plant claimed: *Solenostemon scutellarioides.*

Variety denomination: 'Balflamsira'.

BACKGROUND OF THE INVENTION

The present invention relates to a new and distinct cultivar of Coleus plant botanically known as *Solenostemon scutellarioides* and hereinafter referred to by the cultivar name 'Balflamsira'.

The new cultivar originated in a controlled breeding program in Guadalupe, Calif. during September 2016. The objective of the breeding program was the development of Coleus cultivars with unique foliage coloration and leaf shape, upright growth habit, and good sun tolerance.

The new Coleus cultivar was the result of a self-pollination of COLORBLAZE ROYALE APPLE BRANDY 'ApBran', not patented, characterized by its burgundy brown and chartreuse-colored foliage, and moderately vigorous, compact-upright growth habit. The new cultivar was selected as a single flowering plant within the progeny of the above stated self-pollination during August 2017 in a controlled environment in Guadalupe, Calif.

Asexual reproduction of the new cultivar by terminal stem cuttings since August 2017 in Arroyo Grande, Calif. and West Chicago, Ill. has demonstrated that the new cultivar reproduces true-to-type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balflamsira' as a new and distinct cultivar of Coleus plant:

1. Dark greyed-red and deep yellow-green colored foliage, and
2. Moderately vigorous, upright growth habit.

Plants of the new cultivar differ from plants of the parent primarily in foliage color shades.

Of the many commercially available Coleus cultivars, the most similar in comparison to the new cultivar is Flame-Thrower Serrano 'UF15-6-28', U.S. Plant Pat. No. 30,970. However, in side by side comparisons, plants of the new cultivar differ from plants of 'UF15-6-28' in at least the following characteristics:

1. Plants of the new cultivar have a lighter shade of greyed-red leaf color than plants of 'UF15-6-28';
2. Plants of the new cultivar have more leaf margin lobes than plants of 'UF15-6-28'; and
3. Plants of the new cultivar have a stem color that is mottled with a greyed-red coloration unlike plants of 'UF15-6-28'.

BRIEF DESCRIPTION OF THE PHOTOGRAPHS

The accompanying photographs show, as nearly true as it is reasonably possible to make the same in color illustrations of this type, the overall growth habit and typical foliage characteristics of the new cultivar. Colors in the photographs differ slightly from the color values cited in the detailed description, which accurately describes the colors of 'Balflamsira'. The approximately 3-month-old plants were grown in 4.5-inch pots for 10 weeks in a greenhouse in West Chicago, Ill. Plants were given one pinch one week before transplant.

DETAILED BOTANICAL DESCRIPTION

Figure 1:
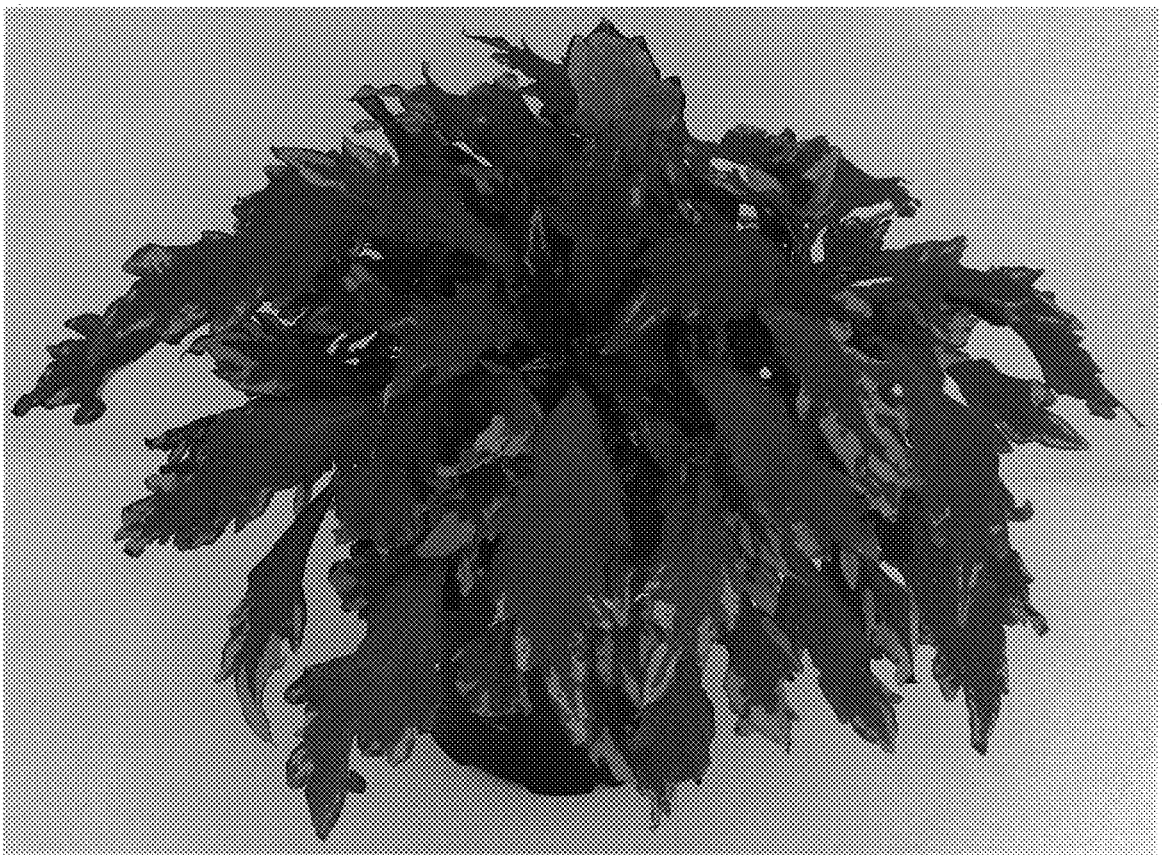
FIG. 1 illustrates a side view of the overall growth habit of 'Balflamsira'.
Figure 2:
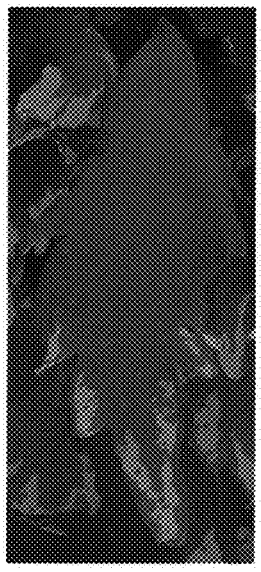
FIG. 2 illustrates a close-up view of an individual leaf of 'Balflamsira'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in January 2020 under natural light conditions in West Chicago, Ill.

The following descriptions and measurements describe approximately 3-month-old plants produced from cuttings from stock plants and grown in a glass-covered greenhouse under conditions comparable to those used in commercial practice. The plants were grown in West Chicago, Ill. in 4.5-inch pots for 10 weeks utilizing a soilless growth medium. Plants were given one pinch one week before transplant. Greenhouse temperatures were maintained at approximately 67° F. to 72° F. (19° C. to 22° C.) during the day and approximately 64° F. to 66° F. (18° C. to 19° C.) during the night. Supplemental lighting was used. Measurements and numerical values represent averages of typical plants.

Botanical classification: *Solenostemon scutellarioides* 'Balflamsira'.

Parentage:

*Female and male parent*.—COLORBLAZE ROYALE APPLE BRANDY 'ApBran'.

Propagation:

*Type cutting*.—Terminal stem.

*Time to initiate roots*.—Approximately 4 to 6 days.

*Time to produce a rooted cutting*.—Approximately 21 to 24 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Moderately vigorous, upright.

*Size*.—Height from soil level to top of plant plane: Approximately 15.5 cm. Width: Approximately 26.0 cm.

*Branching habit*.—Freely branching, pinching not required but improves basal branching. Quantity of lateral branches per plant: Approximately 9.

*Branch*.—Strength: Strong. Shape: Square in cross section. Length of lateral branch: Approximately 7.5 cm. Diameter of lateral branch at central internode: Approximately 5.0 mm. Length of central internode of lateral branch: Approximately 1.0 cm. Texture: Dense minute pubescence. Color of young and mature stems: 146C with mottling of 187A.

Foliage description:

*General description*.—Quantity of leaves per lateral branch: Approximately 12. Fragrance: None. Form: Simple. Arrangement: Opposite.

*Leaves*.—Aspect: Petiole is at an acute angle to stem; leaf blade is perpendicular to stem, and transitions to an obtuse angle with age. Appearance: Matte. Shape: Elliptic. Margin: Lobed. Apex: Acute. Base: Attenuate. Venation pattern: Pinnate. Length of mature leaf: Approximately 9.0 cm. Width of mature leaf: Approximately 3.3 cm. Texture of upper surface: Sparsely pubescent. Texture of lower surface: Sparsely pubescent with moderate pubescence on venation. Pubescence color: A mixture of colorless, transparent and 187A. Color of upper surface of young foliage: 144A, with irregular mottling 183A and 178A to 178B, mottling primarily in center of leaf; venation coloration indistinguishable from leaf lamina. Color of lower surface of young and mature foliage: Closest to 147C with 187A at margins edges; venation coloration indistinguishable from leaf lamina or sometimes tinted with 187A. Color of upper surface of mature foliage: 144A, with an irregular and heavy overlay of 183A and 178A to 178B; venation coloration indistinguishable from leaf lamina.

*Petiole*.—Length: Approximately 3.0 cm. Width: Approximately 2.0 mm. Texture: Moderately pubescent. Pubescence color: A mixture of colorless, transparent and 187A. Color: 146C with mottling of 187A to 187B.

Flowering description: To date, flower development has not been observed on plants of the new Coleus.

Disease and pest resistance: To date, resistance to pathogens and pests common to Coleus has not been observed.

What is claimed is:

1. A new and distinct cultivar of Coleus plant named 'Balflamsira', substantially as herein illustrated and described.

* * * * *